United States Patent
Ganshorn

(10) Patent No.: US 7,402,139 B2
(45) Date of Patent: Jul. 22, 2008

(54) APPLIANCE FOR THE OSCILLOMETRIC ANALYSIS OF THE IMPEDANCE OF THE RESPIRATORY TRACT

(76) Inventor: Peter Ganshorn, Industriestraβe 6 -8, 97618 Niederlauer (DE)

( * ) Notice: Subject to any disclaimer, the term of this patent is extended or adjusted under 35 U.S.C. 154(b) by 155 days.

(21) Appl. No.: 10/597,948

(22) PCT Filed: Feb. 4, 2005

(86) PCT No.: PCT/DE2005/000184

§ 371 (c)(1),
(2), (4) Date: Aug. 14, 2006

(87) PCT Pub. No.: WO2005/077270

PCT Pub. Date: Aug. 25, 2005

(65) Prior Publication Data

US 2007/0161918 A1    Jul. 12, 2007

(30) Foreign Application Priority Data

Feb. 14, 2004   (DE)   ........................ 10 2004 008 057

(51) Int. Cl.
*A61B 5/08* (2006.01)
(52) U.S. Cl. ...................................... 600/533; 600/529
(58) Field of Classification Search ......... 600/529–543, 600/484
See application file for complete search history.

(56) References Cited

U.S. PATENT DOCUMENTS

| | | | | |
|---|---|---|---|---|
| 5,316,002 A | * | 5/1994 | Jackson et al. | 600/463 |
| 5,666,960 A | * | 9/1997 | Fredberg et al. | 600/529 |
| 5,746,699 A | * | 5/1998 | Fredberg et al. | 600/529 |
| 5,882,314 A | * | 3/1999 | Fredberg et al. | 600/529 |
| 6,183,423 B1 | * | 2/2001 | Gaumond et al. | 600/529 |
| 6,287,264 B1 | * | 9/2001 | Hoffman | 600/538 |
| 6,379,311 B1 | * | 4/2002 | Gaumond et al. | 600/529 |
| 6,422,094 B1 | * | 7/2002 | Ganshorn | 73/861.29 |
| 6,440,083 B1 | * | 8/2002 | Fredberg et al. | 600/533 |
| 6,491,641 B1 | * | 12/2002 | Rasmussen | 600/529 |
| 6,723,055 B2 | * | 4/2004 | Hoffman | 600/538 |
| 7,094,206 B2 | * | 8/2006 | Hoffman | 600/529 |
| 7,325,545 B2 | * | 2/2008 | Dellaca' et al. | 128/204.23 |

* cited by examiner

*Primary Examiner*—Charles A. Marmor, II
*Assistant Examiner*—Navin Natnithithadha
(74) *Attorney, Agent, or Firm*—Edwin D. Schindler

(57) ABSTRACT

An apparatus for determining the impedance ($Z_{aw}$) of a patient's respiratory tract, by measuring the alternating pressure (dp) in the region of the patient's mouth after producing an oscillating air pressure signal, includes a mouthpiece, an electroacoustic transducer having a mechanical oscillation system for generating the oscillating air pressure signal, a tube for connecting the electroacoustic transducer to the mouthpiece, a reference resistance for determining the reference impedance ($Z_{ref}$), and a computing device for calculating the impedance ($Z_{aw}$) of the respiratory tract on the basis of the reference impedance ($Z_{ref}$) of the reference resistance, the entire impedance ($Z_{ges}$) and the entire phase angle (Phi). The change in the deflection of the mechanical oscillation system on the electroacoustic transducer, caused by the alternating pressure (dp) of the breathing of the patient, can be measured in a contactless manner using at least one measuring device.

20 Claims, 1 Drawing Sheet

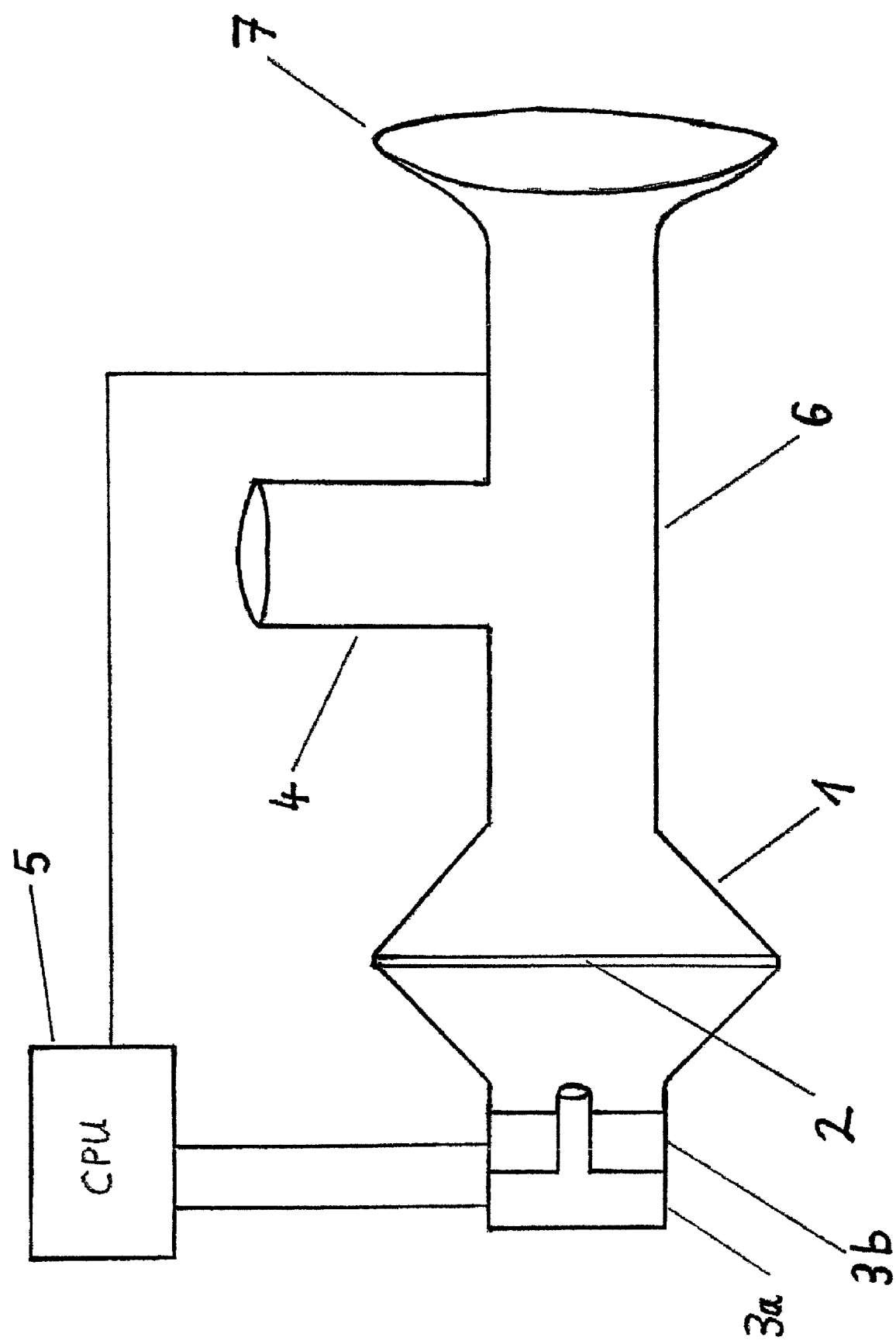

APPLIANCE FOR THE OSCILLOMETRIC ANALYSIS OF THE IMPEDANCE OF THE RESPIRATORY TRACT

BACKGROUND OF THE INVENTION

1. Technical Field of the Invention

The invention relates to an apparatus for determining the impedance ($Z_{aw}$) of the respiratory tract by measuring the alternating pressure (dp) in the region of the mouth of a patient after producing an oscillating air pressure signal. The apparatus comprises of a mouthpiece, an electroacoustic transducer provided with a mechanical oscillation system for generating the oscillating air pressure signal, a tube for connecting the electroacoustic transducer to the mouthpiece, a reference resistance for determining the reference impedance ($Z_{ref}$), and a computing device for calculating the impedance ($Z_{aw}$) of the respiratory tract on the basis of the reference impedance ($Z_{ref}$) of the reference resistance, the total impedance ($Z_{ges}$), and the total phase angle ($\phi$).

The efficiency of a lung is determined by the effectiveness of gas exchange, that is to say in the delivery of oxygen to the blood and the removal of carbon dioxide from the blood. The two processes are dependent on a large number of parameters, such as on the lung volume, on the distribution of respiratory air within the lung, on the surface area of the alveolocapillary membranes, their thickness and diffusion properties, or on the ventilation. All these parameters, in the event of a deviation of the parameters from the norm, may form the causes of disturbances in lung activity.

Of particular medical interest, however, is the resistance of the respiratory tracts. An elevated respiratory tract resistance is one of the main indicators of an abnormal functioning of the lungs, as is demonstrated by, for example, asthmatics and allergies. With the determination of the "respiratory tract impedance", the doctor has a, if not the, fundamental parameter of the lung function. All the known methods for determining the respiratory tract resistance, such as body plethysmography, flow/volume determination, occlusion pressure resistance, among other are indirect measurement methods that require not inconsiderable cooperation of the patient. Only determination of the respiratory tract resistances by means of the oscillatory method permits direct measurement of the respiratory tract resistance without the cooperation of the patient.

The term "impedance" is known from electrical technology and describes the current resistance in an alternating current circuit (alternating current resistance). In an electrical circuit with two poles, on which an alternating current is applied, the alternating current is displaced with respect to the applied current by a particular phase angle. The physically precise description of the phase displacement is possible by means of complex numbers. For a complex number z, in algebraic notation $z=x+iy$, in exponential notation $z=r\,e^{i\phi}$ and in trigonometric notation $z=r\,(\cos\phi+ I\sin\phi)$. A complex number is given by the magnitude $r=|Z|$ and the phase angle $\phi$. In the case of respiratory impedance $Z_{res}$, which represent a resistance as a complex parameter and is also known as total impedance ($Z_{aw}$), model experiments have shown that $Z_{res}$ is also physically adequately defined by these two parameters.

The resistances of the respiratory tract can be termed in analogy to the resistances of an electrical circuit. The real resistance to respiration is always positive and is caused by the frictional losses in gas and tissue. The real respiratory resistance is also known as resistance (flow resistance) and corresponds to the real part (x) of the complex respiration resistance. The trachea and bronchia act as inductive resistances by virtue of the mass inertia of the gases they contain. Because of the compressibility of the air and because of the tissue elasticity, a capacitative resistance component also occurs. The total (in the sense of a vectorial addition) of the inductive and capacitative resistances is the reactance, which makes up the imaginary real part (y) of the complex resistance. The resistance and the reactance are given in [kPa/(l/s)]. The term resistance oscillation (Ros) corresponds to the respiratory impedance $Z_{res}$ at an oscillation frequency.

Since the computing equipment necessary for the analysis of complex numbers only became ready for production at a relatively late stage, the evaluation of the data determined as part of the oscillator resistance measurement at first only referred to the determination of respiration resistance as a real magnitude (German patent 1960 640), which is also termed the oscillatory resistance (Ros).

2. Description of the Prior Art

In the prior art, various methods are known for oscillatory determination of the respiratory tract resistance. Oscillations of 4 to 50 Hz are imposed on the patient's respiratory tract via the mouth with an open or closed nose.

The SIREGNOT FD5 appliance from Siemens superimposes a high frequency oscillation flow of about 10 Hz on the human respiratory frequency of 0.2 to 0.3 Hz. The superimposed oscillation current of 10 Hz is generated by a valveless diaphragm pump with a defined displacement. A plastic tube additionally connected to the mouthpiece with a known radius and a known length is oscillated parallel to the patient's respiratory tract. The tube serves as a reference resistance in the sense of an impedance, which is caused by the inductance of the oscillating air column. The patient can breathe unhindered through this reference tube, the volume of the tube only insignificantly enlarging the dead space. The oscillating volume flow generates an alternating pressure (dp) in the mouth, which is recorded by a microphone. The alternating pressure has a phase displacement ($\phi$) with respect to the volume flow emerging from the generator of the air-pressure signal. After filtering, rectification and smoothing of the analogue voltage signal, the resistance is displayed on the instrument.

The value that can be read on the indicator instrument is calculated by means of a computing device, which is suitable for calculating the respiratory tract impedance ($Z_{aw}$) from the reference impedance ($Z_{ref}$) and the total impedance ($Z_{ges}$) and the total phase angle ($\phi$). The relationship between the total impedance ($Z_{ges}$) and respiratory tract impedance ($Z_{aw}$) and the reference impedance ($Z_{ref}$) is governed by $1/Z_{ges}=1/Z_{aw}+1/Z_{ref}$, if $Z_{aw}$ and $Z_{ref}$ are connected in parallel. By applying the calculating rules for complex numbers, the real part and imaginary part of the respiratory tract impedance ($Z_{aw}$) can be determined. The reference impedance ($Z_{ref}$) is determined by the reference air tube, while the total impedance ($Z_{ges}$) is measured by a pressure tranducer, wherein it should be considered that the volume flow dV/dt remains constant. By virtue of this constancy, the measured alternating pressure at the mouth can be regarded as a measure of the total impedance ($Z_{ges}$). The computing device calculates the respiratory tract impedance ($Z_{aw}$) and the real part of the respiratory tract impedance ($Z_{aw}$) from the given reference impedance ($Z_{ref}$) and the given reference phase angle, and the measured alternating pressure at the mouth as a measure of the total impedance ($Z_{ges}$) and the measured total phase angle.

From the prior art, impulse oscillometry (IOS) is also known, in which an electrical square pulse is transformed by the mechanic properties of the downstream loudspeaker into a mixture of the desired frequencies. A lung function test device operating according to the principle of impulse oscillometry consists of a loudspeaker for generating the test pulses, a T-shaped connector, in which the modulation of the respiratory current is performed by the test signal. An opening of the T-connection leading away from the loudspeaker has a defined resistance with respect to the ambient air, via which the patient can breathe freely. The other T-piece opening leading away from the loudspeaker is connected to a pneumatograph, in which a pressure sensor is integrated. While the pressure sensor permits measurement of the mouth pressure (p), the volume flow rate (V) is measured by means fo the pneumatograph. The measurement results are read as electrical signals. The pressure-flow quotient is the thoracopulmonary impedance of the patient that is to be determined. For calibration of the measurement head, the reference impedance ($Z_{ref}$) is measured at the output of the pressure sensor that is connected downstream of the pneumonograph. For this purpose, a sieve resistance element, which can be designed with different shapes, is measured. German patent 432 63 74 A1 describes a conically flared reference impedance with sieve resistance, which is suitable for the calibration of the pressure and flow measuring equipment of a device for oscillometric measurement of the respiratory tract resistance.

SUMMARY OF THE INVENTION

The object of the invention concerns the determination of the respiratory tract impedance $Z_{aw}$ or $Z_{res}$ of a patient by precise measurement of the total impedance and of the associated phase angle by means of an appliance that is equipped with only one mechanical oscillation system. Herein, detection of the deflection, caused by the patient, of the mechanical oscillation system is intended to be contactless, so that the oscillation system is not disturbed by the measurement.

This object is achieved by the design of an appliance for measurement of the respiratory impedance, which is characterised in that the change in the deflection of the mechanical oscillation system on the electroacoustic transducer, caused by the alternating pressure (dp) of the breathing of the patient, can be measured in a contactless manner by means of at least one measuring device.

The appliance according to the invention serves for calculating the complex respiratory tract resistance $Z_{aw}$ and $Z_{res}$ respectively and consists essentially of an electroacoustic transducer whose mechanical oscillation system serves to generate an oscillating air-pressure signal. The air-pressure signal is transferred via a tube to the mouthpiece of the patient. A reference resistance is also connected to the tube, which serves for determining the reference impedance ($Z_{ref}$). The computing device connected to the reference resistance and the electroacoustic transducer and to the mechanical oscillation system is suitable for carrying out computations with complex numbers as input parameters, such as the Fourier transform (FFT), with the aid of which the data recorded in the time domain can be converted to the frequency domain. The details of the Fourier transform are known to a person skilled in the art.

DETAILED DESCRIPTION OF THE PREFERRED EMBODIMENTS

The gist of the invention is the fact that the alternating pressure (dp) caused by the patient's respiration acts on the mechanical oscillation system of the electroacoustic sound transducer, which serves as loudspeaker and microphone. The mechanical oscillation system, which serves as impulse (loudspeaker) and generates the volume flow dV/dt, is also subject to the pressure fluctuations (dp) caused by the patient's breathing. To register this superimposed pressure fluctuations, the deflections of the mechanical oscillation system are measured. Based on this measurement, the effective volume flow dV/dt required for the resistance calculation can be directly determined as a function of the diaphragm movement.

To demonstrate the effect of the patient's breathing on the oscillation system of the electroacoustic transformer, the use of different techniques is conceivable, which in each case represent special embodiments of the device according to the equipment and are described in the sub-claims provided for this purpose.

It is essential to the invention that the deflection of the mechanical oscillation system caused by the patient's breathing takes place simultaneously with the generation of the oscillating air-pressure signal. Because of the simultaneous detection, on the mechanical oscillation system there occurs the above-mentioned superimposition of oscillations of the generated air-pressure signal and those oscillations caused by the alternating pressure of the patient's breathing In a preferred embodiment of the device according to the invention, the mechanical oscillation system is a flexible diaphragm that consists of a moisture-resistant material or a sheet metal. The material of the membrane should be so composed that it permits the generation and registration of low-frequency oscillations, such as are necessary for the use of the appliance according to the invention.

The electroacoustic transducer used both for the generation and the detection of sound is the centrepiece of the appliance according to the invention. Sound consists of oscillations, which cause density fluctuations in the air and are transmitted thereby. Loudspeakers and microphones are elecroacoustic transducers that can transform the alternating sound pressure, via a mechanical oscillation system (diaphragm) into an electrical voltage.

The diaphragm, as an active element, is set into mechanical oscillation by electrical alternating currents and thereby generates sound waves. In the microphone, the mechanical oscillation system conversely serves to transform sound into voltages and currents of sound frequency. The different electrostatic transducers differ in the absolute value and in the frequency-dependency of the transducer efficiency, but also in its mechanical sensitivity and sound-pressure loading capacity. The use of electroacoustic transducers for the present invention is essentially restricted to electrodynamic, electromagnetic and piezoelectric transducers.

In the electrodynamic transducer, the diaphragm moves a coil in a pot magnet, so that, with the movement, electrical alternating voltages, which are proportional to the sound wave, of tuned frequency are induced in oscillating coil. If a tuned-frequency alternating current flows through the oscillating coil, the coil moves axially in the air gap as a result of the induction, specifically in the rhythm of the alternating current. The diaphragm fastened to the oscillating coil is moved sympathetically, and in the process excites the surrounding air to acoustic oscillations. A variant of the dynamic microphone with oscillating coil is the ribbon microphone, in which the diaphragm and moving coil are replaced by a ribbed aluminium ribbon, which oscillates in the magnetic field in the rhythm of the sound waves.

In the electromagnetic transducer, the movement of the magnetic diaphragm changes the air gap of a magnet such that the magnetic flux in the magnet yoke is modulated and an electrical voltage is induced in a winding.

In the piezoelectric transducer, the deformation of a crystal with piezoelectric properties effects a displacement of the charge structure and of the piezoelectrically generated surface charge, whose electrical voltage is proportional to the sound pressure. Conversely, piezoelectric crystals, on electrical charging, undergo a thickness change, which is converted into audio-frequency oscillations of the diaphragm.

From the above-described features of the different transducer types, it results that the deflection of the diaphragm can be measured inductively, capacitatively or optically according to the transducer used.

In an alternative embodiment, the change of deflection of the mechanical oscillation system, as a result of the patient's breathing, is detected by a laser. For this purpose, reflectors or detectors are mounted on the diaphragm at one or more points. The beam of the stationary laser registers the movement of the diaphragm and thereby detects its oscillations. The technical details of this measurement are known to a person skilled in the art.

For the design of the reference resistance, essentially two alternative embodiments are conceivable. The first embodiment consists of a cylindrical air tube, the internal resistance of which becomes larger with increasing length. An alternative embodiment relates to an air tube, which is conically flared at the end facing away from the mouthpiece, a sieve resistance being inserted into this opening. The advantages and special features of this embodiment are taken from German Patent 432 63 74 A1. It is provided that the reference resistances are removable and interchangeable for hygienic purposes.

In a special embodiment, the respiratory tract mask is designed such that, in the region in which the respiratory tract mask is introduced into the connecting tube, the external diameter is less than the internal diameter of the connecting tube. In this manner, the respiratory tract mask lies with slight tension against the inside of the connecting tube, such that the two components of the appliance according to the invention are connected in an airtight manner to one another.

In an alternative development of the respiratory tract mask, the part that can be introduced into the connecting tube has two or more openings laterally. The openings are offset with respect to one another, so that they do not lie directly opposite one another. The openings can be covered by means of a perforated liquid-absorbent material. The material is preferably applied to the inside of the respiratory tract mask.

In a further development of the appliance according to the invention, it is provided that the computer unit is assigned a monitor or an output unit in the form of a printer. The measured values (resistance, reactance or phase angle) can in this case be plotted on a diagram and graphically processed and analysed on the monitor. A printer connected to the device according to the invention permits print out of the data.

BRIEF DESCRIPTION OF THE DRAWING FIGURES

Further details and features of the invention are explained below in greater detail with reference to an example. The illustrated example is not intended to restrict the invention, but only to explain it.

DETAILED DESCRIPTION OF THE DRAWING FIGURES

FIG. 1 shows a schematic view of the construction of the appliance according to the invention for determining the breathing tract impedance. The most important component from a technical point of view is the electroacoustic transducer 1 with the mechanical oscillation system 2, which serves both for generating an oscillating air pressure signal as well as for detection of the alternating pressure (dp) caused by the patient's breathing. The alternating pressure (dp) caused by the patient's breathing results from the patient whose mouth is applied to the mouthpiece 7. The connection between the removable mouthpiece 7 and the electroacoustic transducer 1 is produced by the tube 6. A branch from the tube 6 forms the removable and interchangeable reference resistance 4. In the simplest embodiment, the reference resistance 4 consists of a cylindrical tube, through which the patient can breathe freely. The impedance of the tubular reference resistance 4 is caused by the inductance of the oscillating air column. The patient can breathe unhindered via the reference resistance 4, without the volume of the tube significantly enlarging the dead space. The alternating pressure (dp) caused by the breathing of the patient sets the mechanical oscillating system 2, which simultaneously serves to generate the oscillating air pressure signal, into oscillation. In comparison to the oscillating air pressure signal generated first, by virtue of the superimposition of the oscillations, a deviation occurs, which characterises the patient's breathing and is detected by further components of the microphone 3b.

A central computer unit is connected to the generator of the oscillating air pressure signal, which takes the form of a loudspeaker, and the microphone components 3b, as well as to the reference resistance 4. The central computer unit permits the control of the loudspeaker 3a and the registration of the data registered by the microphone 3b, as well as the evaluation thereof. The computer unit operates taking into account the complex computing rules that are known to a person skilled in the art. Not illustrated is the monitor and/or printer that is connected to the central computer unit.

The invention claimed is:

1. An apparatus for determining impedance ($Z_{aw}$) of a patient's respiratory tract by measuring alternating pressure (dp) in a region of the patient's mouth after producing an oscillating air pressure signal, comprising:
   a mouthpiece;
   an electroacoustic transducer having an oscillation system for generating an oscillating air pressure signal;
   a tube for connecting said electroacoustic transducer to said mouthpiece;
   a reference resistance for determining a reference impedance ($Z_{ref}$);
   computing means for calculating impedance ($Z_{aw}$) of a patient's respiratory tract based upon said reference impedance ($Z_{ref}$) of said reference resistance, total impedance ($Z_{ges}$) and total phase angle ($\Phi$); and,
   means for contactlessly measuring change in deflections of said oscillation system of said electroacoustic transducer caused by alternating pressure (dp) of the patient's breathing.

2. The apparatus for determining impedance ($Z_{aw}$) of a patient's respiratory tract according to claim 1, wherein said electroacoustic transducer is a loudspeaker with said oscillation system of said electroacoustic transducer forming an oscillation system of a microphone for said loudspeaker with measurement of said change in deflections of said oscillation system taking place during generation of said oscillating air pressure signal.

3. The apparatus for determining impedance ($Z_{aw}$) of a patient's respiratory tract according to claim 1, wherein said oscillation system is a movable, stiff diaphragm comprising a moisture-resistant material.

4. The apparatus for determining impedance ($Z_{aw}$) of a patient's respiratory tract according to claim 1, wherein said oscillation system is a movable, stiff diaphragm comprising sheet metal.

5. The apparatus for determining impedance ($Z_{aw}$) of a patient's respiratory tract according to claim 1, wherein said electroacoustic transducer is an electro-dynamic transducer.

6. The apparatus for determining impedance ($Z_{aw}$) of a patient's respiratory tract according to claim 1, wherein said electroacoustic transducer is an electromagnetic transducer.

7. The apparatus for determining impedance ($Z_{aw}$) of a patient's respiratory tract according to claim 1, wherein said electroacoustic transducer is a piezoelectric transducer.

8. The apparatus for determining impedance ($Z_{aw}$) of a patient's respiratory tract according to claim 1, wherein said electroacoustic transducer is piezoresistive transducer.

9. The apparatus for determining impedance ($Z_{aw}$) of a patient's respiratory tract according to claim 1, wherein said means for contactlessly measuring change in deflections of said oscillation system is carried out via inductive measuring means.

10. The apparatus for determining impedance ($Z_{aw}$) of a patient's respiratory tract according to claim 9, wherein said inductive measuring means includes an induction-generating conductor applied to said oscillation system and a positively fixed induction coil installed proximate to said induction-generating conductor.

11. The apparatus for determining impedance ($Z_{aw}$) of a patient's respiratory tract according to claim 1, wherein said means for contactlessly measuring change in deflections of said oscillation system is carried out via capacitative measuring means.

12. The apparatus for determining impedance ($Z_{aw}$) of a patient's respiratory tract according to claim 11, wherein said capacitative measuring means comprises an electrically conductive element acting on said oscillation system with a positionally fixed electrode forming a capacitor for capacitative measurement of the change of said deflections of said oscillation system.

13. The apparatus for determining impedance ($Z_{aw}$) of a patient's respiratory tract according to claim 1, wherein said means for contactlessly measuring change in deflections of said oscillation system is carried out via optical measuring means.

14. The apparatus for determining impedance ($Z_{aw}$) of a patient's respiratory tract according to claim 13, wherein said optical measuring means comprises an optical detector or reflector applied to said oscillation system at, at least, one point onto which a laser beam is directed.

15. The apparatus for determining impedance ($Z_{aw}$) of a patient's respiratory tract according to claim 1, wherein said means for contactlessly measuring change in deflections of said oscillation system is carried via piezoelectric measuring means.

16. The apparatus for determining impedance ($Z_{aw}$) of a patient's respiratory tract according to claim 1, wherein said reference resistance includes an air tube open at a first end with a second end of said air tube being connected to said mouthpiece and has a calibrated, predeterminable reference impedance ($Z_{ref}$).

17. The apparatus for determining impedance ($Z_{aw}$) of a patient's respiratory tract according to claim 16, wherein said air tube forming said reference resistance is cylindrically flared at said first end facing away from said mouthpiece with said air tube being connected to a sieve resistance.

18. The apparatus for determining impedance ($Z_{aw}$) of a patient's respiratory tract according to claim 16, wherein said tube forming said reference resistance is conically flared at said first end facing away from said mouthpiece with said air tube being connected to a sieve resistance.

19. The apparatus for determining impedance ($Z_{aw}$) of a patient's respiratory tract according to claim 1, wherein said mouthpiece is a breathing mask for enclosing the patient's mouth and nose openings in an airtight manner.

20. The apparatus for determining impedance ($Z_{aw}$) of a patient's respiratory tract according to claim 1, wherein said computing means for calculating impedance ($Z_{aw}$) of a patient's respiratory tract includes a monitor and an output device comprising a printer.

* * * * *